United States Patent [19]

Kitayama

[11] Patent Number: 4,872,217
[45] Date of Patent: Oct. 10, 1989

[54] EYE MASK

[76] Inventor: Hidehiro Kitayama, 2-22-11, Yanagibashi, Tokyo, Japan

[21] Appl. No.: 167,161

[22] Filed: Mar. 11, 1988

[30] Foreign Application Priority Data

Mar. 20, 1987 [JP] Japan .................................. 62-39928

[51] Int. Cl.⁴ ............................................... A61F 9/04
[52] U.S. Cl. .............................................. 2/15; 2/433
[58] Field of Search ..................... 2/15, 433, 426, 440, 2/441, 9, 206, 171.2, 439

[56] References Cited

U.S. PATENT DOCUMENTS

| 1,959,915 | 5/1934 | Guthrie | 2/433 X |
| 2,305,080 | 12/1942 | Hemphill et la. | 2/15 |
| 2,537,768 | 1/1951 | Laporte | 2/15 |
| 2,946,133 | 7/1960 | Williams | 2/15 X |
| 3,895,397 | 7/1975 | Douglas | 2/428 |
| 4,649,908 | 3/1987 | Ghaly | 2/15 X |

FOREIGN PATENT DOCUMENTS 0372473  3/1907  France .................................... 2/433

Primary Examiner—Peter Nerbun
Attorney, Agent, or Firm—Cislo & Thomas

[57] ABSTRACT

This invention relates to an eye mask comprising a main member being formed by a plate like element, a long rib portion being formed along to an inner edge portion of said main member, and a band member being connected to both ends of said main member, whereby said long rib portion contacts a periphery of eye, and good sleep is possible since said main member does not directly contatct the eyeball.

1 Claim, 2 Drawing Sheets

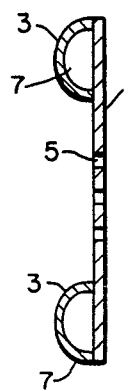
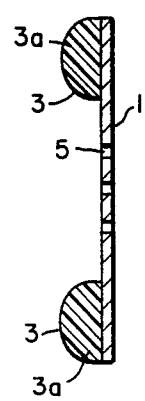
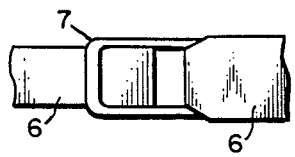
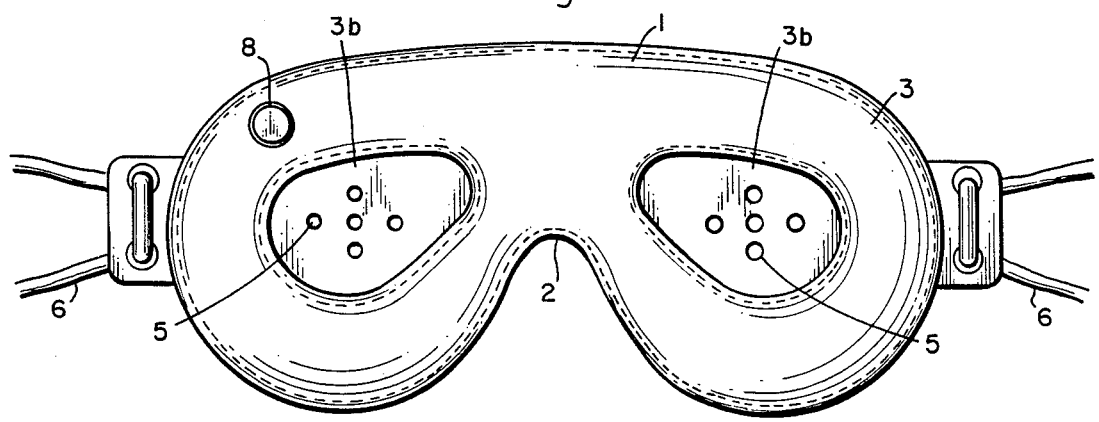
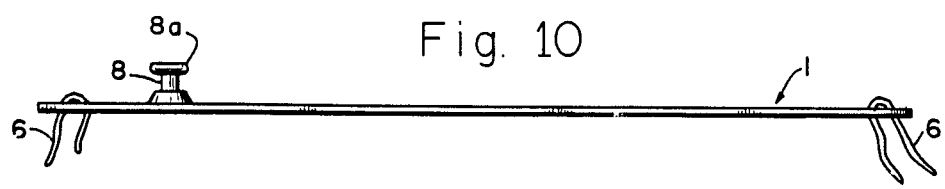
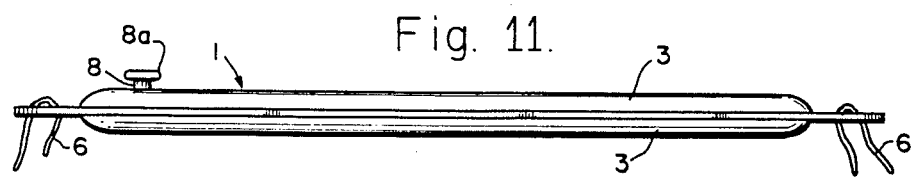

EYE MASK

BACKGROUND OF THE INVENTION

This invention relates to an eye mask, particularly to an improvement for permitting good sleep such that the mask fits comfortably on a face without directly contacting with an eyeball of a user.

Previously, many kinds of eye masks were developed. As shown in the drawing FIGS. 1 to 4, note Japanese laid open utility model No. 61-34221/1986 and Japanese laid open utility model No. 61-34222/1986.

First of all, in the case of Japanese laid open utility model 6-34221, an eye bag 10 including a liquid material is mounted to an eye covering portion of mask member 1 as shown in FIGS. 1 and 2, wherein said eye bag 10 is transformed.

Further, in the case of Japanese laid open utility model No. 61-34222, a cool material 11 is housed in a main portion without a nose portion of mask member 1.

However, there are many difficulties in said constructions of Japanese laid open utility model Nos. 61-34221 and 34222. Namely, in the former, said eye bag 10 is directly contacted with eyeball 12, whereby an eyeball 12 is pressed, and said eye bag 10 becomes an obstacle for a good sleep. Further, in the latter, said cool material 11 is directly contacted with an eyeball, whereby good sleep is inhibited.

SUMMARY OF THE INVENTION

It is an object of the present invention to provide a highly effective eye mask for obviating the above described disadvantages. For achieving the object, the present invention provides an eye mask comprising a main member being formed by a plate, a long rib portion being formed along to an inner edge portion of said main member, and a band member being connected to both ends of said main member, whereby said long rib portion contacts a periphery of an eye, and good sleep is possible since said main member does not directly contact the eyeball.

DESCRIPTION OF THE DRAWINGS

FIG. 6 shows a cross sectional view according to A—A line of FIG. 5,

FIG. 7 shows a cross sectional view of another embodiment of FIG. 6,

FIG. 8 shows a front view of a part of band member,

FIG. 9 shows a front view of another embodiment of eye mask of the present invention, FIG. 10 shows a flat plan view of FIG. 9 when air is not supplyed thereinto, FIG. 11 shows a flat plan view of FIG. 9 when air is supplied thereinto.

DESCRIPTION OF THE PREFERRED EMBODIMENT

Figure 1:
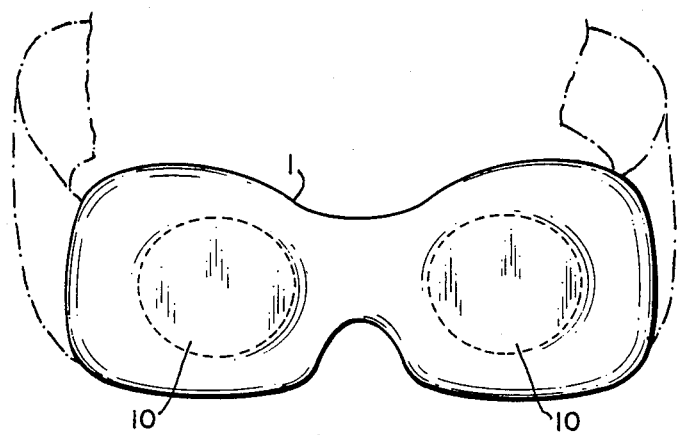
FIG. 1 shows a front view of an eye mask of a conventional type.
Figure 2:
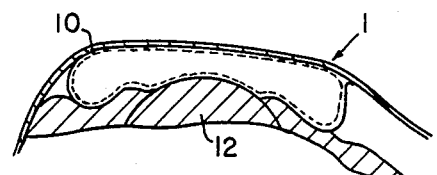
FIG. 2 shows a cross sectional view of a part of FIG. 1.
Figure 3:
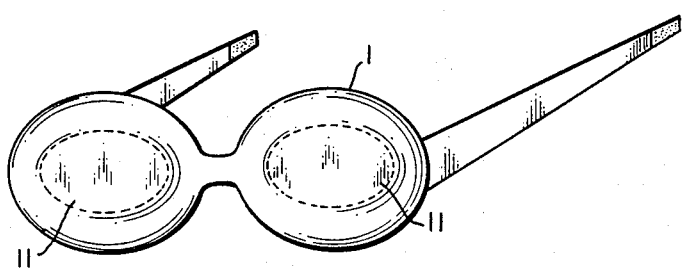
FIG. 3 shows a front view of an eye mask of a conventional type.
Figure 4:
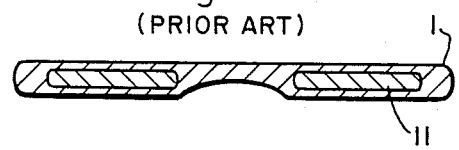
FIG. 4 shows a cross sectional view of a part of FIG. 3.
Figure 5:
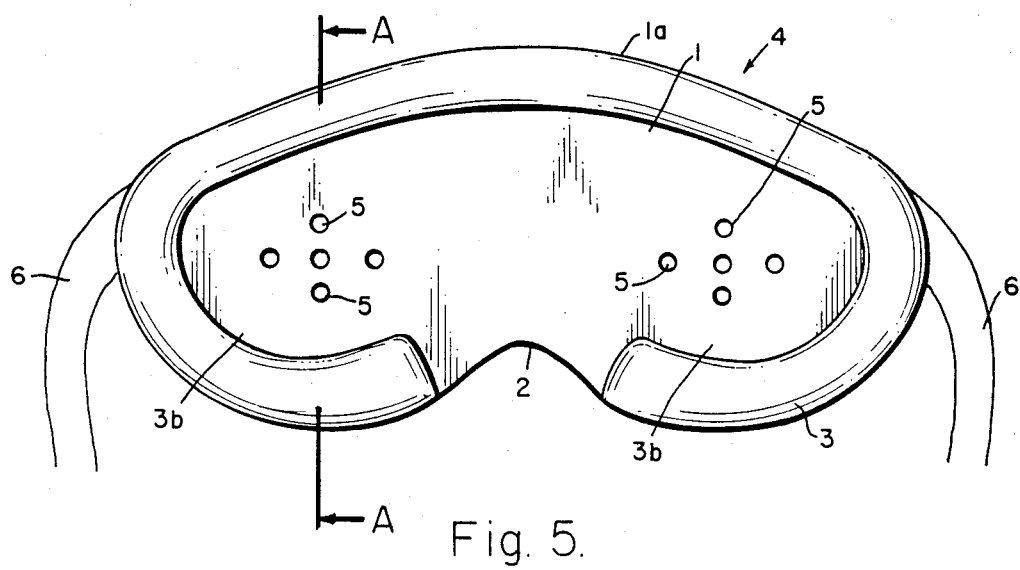
FIG. 5 shows a back portion of eye mask of the present invention.

Reference is now made to the accompanying drawings showing certain preferred embodiments of the present invention. In FIGS. 5-7, numeral 1 is a main member being made of a flexible plate form such as, for example, vinyl and so on, said main member 1 is formed and has an almost oval shape, a nose contacting portion 2 is formed in a lower portion of said main member 1.

A long rib portion 3 having a convex cross sectional portion is integrally formed along an outer peripheral edge portion 1a, a soft material 3a such as polyurethane rubber form is included with said long rib portion 3 as shown in FIG. 7. Said long rib portion 3 is not formed to said nose contacting portion 2 which is definitely in contact with a face when the eye mask 4 is worn on said face. A plurality of small holes 5 are formed for an eyeball to see and correspond to the position of said eyeball when said eye mask is attached to said face, whereby a light from outside passes through said small holes 5 and a user can see slightly through said small holes 5.

Band members 6 are integrally connected to both ends of said main member 1. Both ends of said band members 6 are connected by a connecting member 7 which allow an adjustment of a length thereof.

Further, said main member 1 and long rib member 3 can be made of leather or synthetic leather. Their color is preferably black.

The construction of said long rib member 3 is not limited to said soft material which is enclosed in said long rib member 3 as shown in FIG. 7. For example, as shown in FIG. 6, a hollow portion 7 in said long rib member 3 is filled by an air, oil, cooling material or carbonic acid gas instead of said soft material. Said carbonic acid gas is obtained by a water bag (not shown) and chemicals for generating said long rib member 3, wherein said long rib member 3 is expanded from a flat condition by said carbonic acid gas generated when said water bag is torn.

Further, carbonic acid gas can be put into said long rib member 3 originally.

Further, a heating means (not shown), can be used by connecting said heating means to a cigarette adapter of a car, whereby said eye mask can be heated and used while in a car.

Referring now to using said eye mask; When wearing said eye mask 4, said long rib member 3 is in contact with the face, said eyeball corresponding portions 3b are not in contact with said eyeball of the user of this eye mask since a height of said long rib member 3 is about 0.5 mm–10 mm, whereby the wearer is able to get a good sleep without stimulating his eyeball.

Further, it is very comfortable to heat or cool said long rib member 3 when the eye mask 4 is attached to the face in either the summer season or winter season.

As an another embodiment of the present invention, I disclose a construction as shown in FIGS. 9, 10 and 11. Sheet members 3 are shown in FIGS. 9 and 11. In FIG. 11, both first and second sheet members may be seen. A pair of eyeball corresponding portions 3b is formed by a film material having small holes 5, and an inlet member 8 is formed to cooperate with valve 8a detachably mounted thereto, whereby it is possible to supply air or oil or the like between said sheet member 3 for enlargement thereof as shown in FIG. 11.

Further, a detailed explanation is omitted by using the same reference numerals as said construction of FIG. 5.

According to the present invention, one may obtain advantages as follows:

1. Since a long rib member is formed along a peripheral edge portion of a main member, the eyeball of a user of an eye mask is not in contact directly with a main member, whereby the wearer is able to get a good sleep without stimulation to said eyeball.

2. The invention is comfortable to wear in all seasons by heating or cooling a long rib portion.

3. The wearer is able to see outside while using this eye mask through small holes, whereby it is very convenient to use this eye mask in a car while parked.

What we claimed is:

1. An eye mask for placement on the human face for sleeping purposes comprising the combination of:
first and second air impermeable sheet members sealed along the periphery thereof and adapted to form an air chamber therebetween; valve means communicating said chamber to the exterior of said eye mask, whereby air may be introduced into said chamber, said air impermeable sheet members having a mask configuration and spaced non-air inflated chamber portions corresponding in size and location to the eyes on a human face and having a plurality of apertures in each of said portions; and means on either side of said mask for attachment to the human face of a wearer of said eye mask.

* * * * *